United States Patent
Woolston et al.

(10) Patent No.: US 8,617,127 B2
(45) Date of Patent: *Dec. 31, 2013

(54) MEDICAMENT INJECTION APPARATUS

(75) Inventors: Robert Woolston, Warwick (GB);
Shane Alistair Day, Warwick (GB);
Christopher Nigel Langley,
Warwickshire (GB); **Robert Frederick
Veasey**, Warwickshire (GB)

(73) Assignee: DCA Design International Limited,
Warwick (GB)

( * ) Notice: Subject to any disclaimer, the term of this patent is extended or adjusted under 35 U.S.C. 154(b) by 784 days.

This patent is subject to a terminal disclaimer.

(21) Appl. No.: 10/315,165

(22) Filed: Dec. 10, 2002

(65) Prior Publication Data

US 2003/0114801 A1    Jun. 19, 2003

(30) Foreign Application Priority Data

Dec. 18, 2001  (GB) .................................. 0130139.9

(51) Int. Cl.
*A61M 5/00*    (2006.01)
(52) U.S. Cl.
USPC .......................................... 604/246; 604/151
(58) Field of Classification Search
USPC .................. 604/131, 151, 152, 154, 141; 128/DIG. 1, DIG. 12, DIG. 13
See application file for complete search history.

(56) References Cited

U.S. PATENT DOCUMENTS

| | | | |
|---|---|---|---|
| 3,858,581 A | 1/1975 | Kamen | |
| 3,871,361 A | 3/1975 | Kamen | |
| 5,755,692 A | 5/1998 | Manicom | |
| 5,989,221 A | 11/1999 | Hjertman | |
| 6,248,090 B1 | 6/2001 | Jensen et al. | |
| 6,620,133 B1 * | 9/2003 | Steck ............................ | 604/131 |
| 2003/0114800 A1 | 6/2003 | Veasey et al. | |

FOREIGN PATENT DOCUMENTS

| | | |
|---|---|---|
| EP | 0 293 958 A1 | 12/1988 |
| EP | 362 484 A | 4/1990 |
| WO | WO 97/14459 | 4/1997 |
| WO | WO 97/14459 A1 | 4/1997 |
| WO | WO 97/30741 * | 8/1997 |
| WO | WO 97/30742 * | 8/1997 |
| WO | WO 99/15214 | 4/1999 |

\* cited by examiner

*Primary Examiner* — Kevin C Sirmons
*Assistant Examiner* — Phillip Gray
(74) *Attorney, Agent, or Firm* — Oliff & Berridge, PLC

(57) ABSTRACT

A medicament injection device in which the time elapsed is calculated from the end of a predetermined period during which medicament is permitted to disperse subsequent to completion of an injection stroke. The medicament injection device is particularly suitable for use by those with diabetes in which once a desired dosage of medicament has been selected and expelled from the medicament cartridge into the body of the patient, the injected medicament is allowed to disperse locally from the injection site within the patient's body before the needle arrangement is removed from the patient's body.

10 Claims, 1 Drawing Sheet

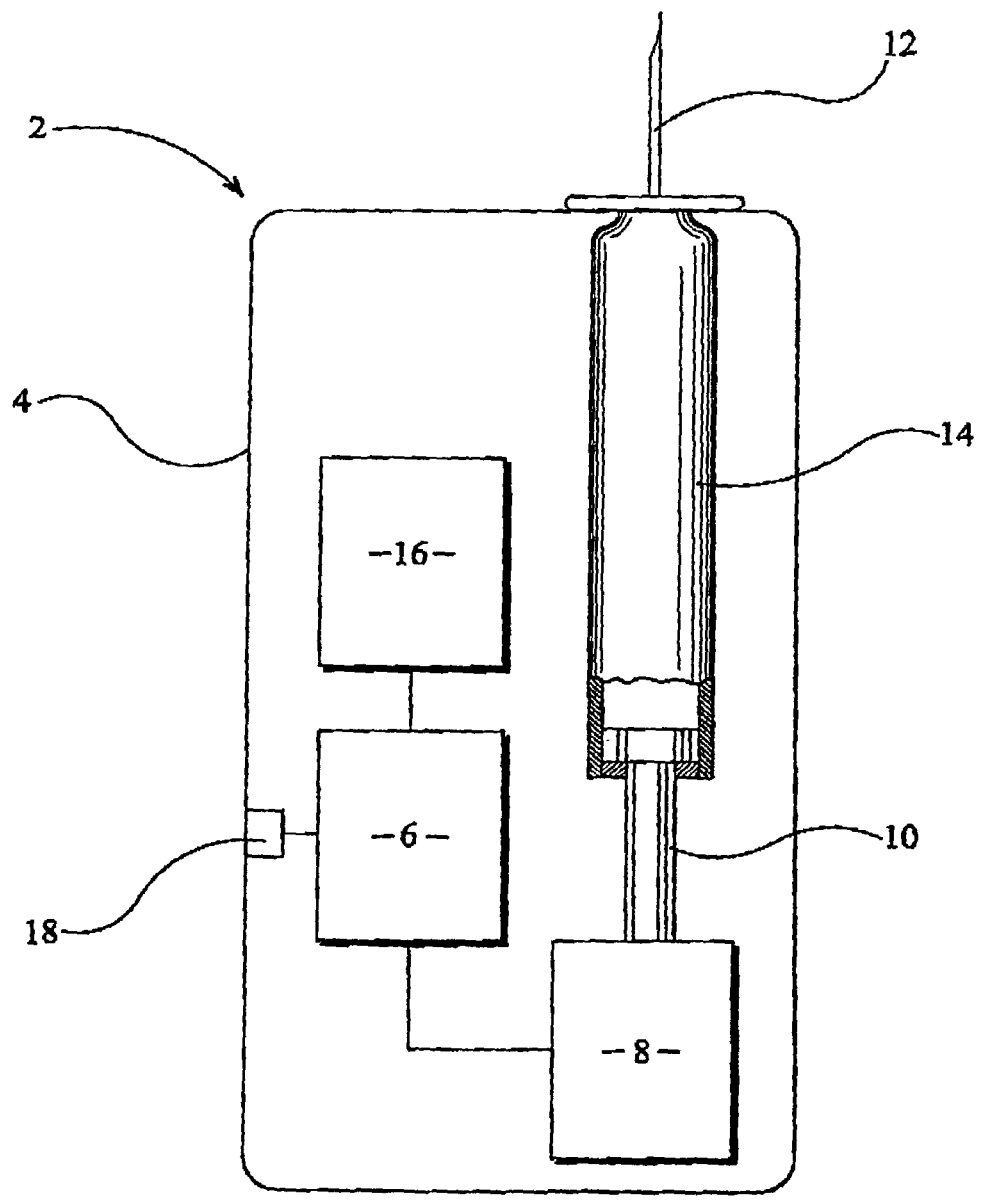

MEDICAMENT INJECTION APPARATUS

FIELD OF THE INVENTION

The disclosure relates to a medicament injection apparatus. In particular, but not exclusively, the disclosure has application for electronically controlled injection apparatus whereby self-administration of a dose of medicament is enabled.

BACKGROUND TO THE INVENTION

Such apparatus generally utilize a medicament cartridge in which a medicament is stored and comprise a microprocessor that controls a drive mechanism to deliver a controlled dosage of medicament through a needle arrangement. The apparatus are small enough readily to be carried about by a user. As such, the apparatus is particularly suitable for use by those with diabetes.

The disclosure is also suitable for other kinds of medicament injection apparatus, for example injection apparatus in which though the dose setting and dose delivery are purely mechanical in character a timer is actuated following completion of a dose delivery stroke to indicate a time elapsed since completion of dose delivery stroke.

In each case, in use, once a desired dosage of medicament has been selected a needle unit of the medicament injection apparatus is inserted into a body of a patient. The drive mechanism is then actuated to cause the selected dosage of medicament to be expelled from the medicament cartridge into the body of the patient.

However, it is necessary once the injection has been made to allow the injected medicament to disperse locally from the injection site within the patient's body before removing the needle arrangement from the patient's body.

It is considered to be a problem that in known medicament injection devices the injection interval, that is the time elapsed since a previous injection, is measured following completion of a delivery stroke rather than from dispersion of the injected medicament.

SUMMARY

According to a first aspect of the disclosure a medicament injection device in which the time elapsed following an injection operation is calculated from the end of a predetermined period during which medicament is permitted to disperse subsequent to completion of an injection stroke.

This has as an advantage that the injection interval is measured from the end of the dispersion period.

Preferably, the medicament injection apparatus provides a signal following completion of the injection operation. This has the advantage that a user will not inadvertently remove the medicament injection apparatus until after the medicament has been allowed to disperse.

According to a second aspect of the disclosure, a method of operation of a medicament injection apparatus comprising a processor having a timer, a medicament cartridge containing medicament, a needle unit to allow medicament to be expelled from the medicament cartridge and a drive means to cause medicament to be expelled from the medicament cartridge comprising the steps of
  i) operating the drive means to expel medicament from the medicament cartridge;
  ii) upon completion of step i) starting a timer to measure a predetermined period;
  iii) upon completion of step ii) resetting the timer to measure the time elapsed since step ii).

Preferably, step ii) also includes upon completion of step ii) causing a signal to be emitted.

Preferably, the method further includes concurrent with step iii) displaying the time elapsed since step ii).

BRIEF DESCRIPTION OF THE DRAWING

The disclosure will now be described, by way of example only, with reference to the accompanying drawing in which;
  FIG. 1 shows schematically an arrangement in accordance with the present invention.

DETAILED DESCRIPTION OF THE EMBODIMENTS

Referring to the Figure, a schematic arrangement of a medicament injection device according to the present invention is disclosed. The medicament injection device 2 comprises a housing 4, a control unit or microprocessor 6, a drive mechanism providing a drive means 8, a piston 10 and a needle unit 12. A medicament cartridge 14, which is preferably replaceable, is located between the piston 10 and the needle unit 12. The medicament cartridge 14 includes a closure at a first end adapted to be pierced by the needle unit and a moveable plunger located towards a second end of the medicament cartridge and adapted to be driven by the piston 10 towards the first end of the medicament cartridge 14.

The control unit or microprocessor 6 includes a timer. In use, a dosage of medicament to be injected is set. The drive means 8 is the actuated to drive the piston 10. The drive means 8 may be actuated mechanically or under the control of the control unit or microprocessor 6. Medicament from within the medicament cartridge 14 is the expelled from the medicament injection device 2.

In the illustrated embodiment, the microprocessor 6 operates the drive means 8 to advance the piston 10. However, in an alternative embodiment, the drive means may be operated manually to advance the piston. In this latter case, the microprocessor monitors the operation of the drive means. In each case, the piston is advanced to expel a dosage of medicament from within the medicament cartridge.

The medicament injection device 6 may also include other elements for fulfilling further functions as required and known in the art.

The timer associated with the control unit or microprocessor 6 is actuated on completion of movement of the piston 10—the injection stroke. A predetermined period of time is then allowed to lapse to permit dispersion of the medicament within the patient. On completion of this first time period, the timer is reset to zero and actuated once more. The timer now records the injection interval in accordance with the present invention.

The medicament injection apparatus 2 may additionally incorporate a display 16. The display may conveniently comprise an LCD display. The display 16 may be used to indicate the duration of the injection interval.

The medicament injection apparatus 2 may further incorporate a signaling device 18, such as a sounder, to signal to the user that the dispersion period has elapsed and that the needle unit may be removed. Alternatively, the user may take the indication of the injection interval on the display 16 as sufficient indication that the dispersion period has elapsed.

A user of the medicament injection device 6 will first operate the medicament injection device 6 to select a dosage of medicament to be injected by the medicament injection device 6. The needle unit 12 will then be inserted into a body of the patient to allow the medicament to be injected. The medicament injection device 6 is then operated to cause the piston 10 to advance.

The user must then allow a short period to elapse to allow the medicament to disperse. If the needle unit 12 is removed too quickly the medicament will escape through the needle wound resulting in an incorrect dosage of medicament having been administered. Thus, when a predetermined time has elapsed following the injection stroke the microprocessor 6 causes a signal, either visual, audible or both, to be given indicating that the needle unit 12 may be removed from the patient. A sounder 18 may be used to generate the signal if an audible signal is required.

At the same time as the signal is given, the microprocessor 6 resets the timer to zero and then measures the time elapsed since the signal was given. The time elapsed since the signal was given may be indicated to a user on the display 16.

What is claimed is:

1. A medicament injection device suitable for the self-administration of a medicament, the device comprising:
   a sounder,
   wherein upon completion of an injection stroke, a predetermined period of time is allowed to lapse during which medicament is permitted to disperse, and
   wherein the sounder generates an audible signal indicating to the user when to remove the needle from the body after said dispersion of an injected medicament;
   a drive means; and
   a timer having a control means,
   wherein the timer measures the predetermined period from completion of operation of the drive means and the control means resets the timer upon completion of the predetermined period to measure a time elapsed following the injection operation.

2. The medicament injection device according to claim 1, wherein the medicament injection device signals an end of an injection operation.

3. The medicament injection device according to claim 1, wherein the medicament injection device further includes a display to indicate the time elapsed following the injection operation.

4. The medicament injection device according to claim 2, wherein the medicament injection device further includes a display to indicate the time elapsed following the injection operation.

5. The medicament injection device according to claim 1, wherein the medicament injection device further includes means to indicate the end of the predetermined period from completion of operation of the drive means.

6. The medicament injection device according to claim 2, wherein the medicament injection device further includes means to indicate the end of the predetermined period from completion of operation of the drive means.

7. The medicament injection device according to claim 3, wherein the medicament injection device further includes means to indicate the end of the predetermined period from completion of operation of the drive means.

8. The medicament injection device according to claim 4, wherein the medicament injection device further includes means to indicate the end of the predetermined period from completion of operation of the drive means.

9. The method of operation of the medicament injection device according to claim 1, wherein the device includes a medicament cartridge for housing the medicament, a sounder, and a drive means, said method comprising the steps of:
   i) operating the drive means to expel medicament from the medicament cartridge;
   ii) upon completion of step i) starting a timer to measure a predetermined period during which medicament is permitted to disperse and causing the sounder to generate an audible signal indicating to a user when to remove the needle from the body after the dispersion of the injected medicament; and
   iii) wherein upon completion of step ii) the timer is reset to measure the time elapsed since the completion of step ii).

10. The method according to claim 9, wherein concurrent with step iii) the time elapsed since step ii) is displayed.

* * * * *